United States Patent
Lv et al.

(10) Patent No.: US 10,315,998 B2
(45) Date of Patent: Jun. 11, 2019

(54) AMIDE COMPOUND AND THE PREPARATION METHOD AND USE THEREOF

(71) Applicant: SHENYANG SINOCHEM AGROCHEMICALS R&D CO., LTD, Liaoning (CN)

(72) Inventors: Liang Lv, Liaoning (CN); Gang Wang, Liaoning (CN); Zhonggang Shan, Liaoning (CN); Jiyong Liu, Liaoning (CN); Qin Sun, Liaoning (CN); Junfeng Wang, Liaoning (CN); Bin Li, Liaoning (CN)

(73) Assignee: SHENYANG SINOCHEM AGROCHEMICALS R&D CO., LTD., Liaoning (CN)

( * ) Notice: Subject to any disclaimer, the term of this patent is extended or adjusted under 35 U.S.C. 154(b) by 0 days.

(21) Appl. No.: 15/551,401

(22) PCT Filed: May 4, 2016

(86) PCT No.: PCT/CN2016/080952
§ 371 (c)(1),
(2) Date: Aug. 16, 2017

(87) PCT Pub. No.: WO2016/177318
PCT Pub. Date: Nov. 10, 2016

(65) Prior Publication Data
US 2018/0029991 A1 Feb. 1, 2018

(30) Foreign Application Priority Data
May 6, 2015 (CN) .......................... 2015 1 0226412
May 6, 2015 (CN) .......................... 2015 1 0226786

(51) Int. Cl.
| | |
|---|---|
| A01N 43/56 | (2006.01) |
| C07D 231/16 | (2006.01) |
| A01N 43/78 | (2006.01) |
| C07D 231/14 | (2006.01) |
| C07D 277/56 | (2006.01) |

(52) U.S. Cl.
CPC .......... *C07D 231/16* (2013.01); *A01N 43/56* (2013.01); *A01N 43/78* (2013.01); *C07D 231/14* (2013.01); *C07D 277/56* (2013.01)

(58) Field of Classification Search
CPC ...... A01N 43/56; A01N 43/78; C07D 231/16; C07D 277/22
USPC ...................... 514/365, 406; 548/146, 356.1
See application file for complete search history.

(56) References Cited

U.S. PATENT DOCUMENTS 5,045,554 A   9/1991  Alt et al.
2009/0163569 A1  6/2009  Tobler et al.

FOREIGN PATENT DOCUMENTS

| CN | 1043127 A | 6/1990 |
|---|---|---|
| CN | 101979375 A | 2/2011 |
| CN | 104649973 A | 5/2015 |
| JP | S5657776 A | 5/1981 |
| JP | S62249975 A | 10/1987 |
| WO | 2015074614 A1 | 5/2015 |

OTHER PUBLICATIONS

International Search Report for PCT/CN2016/080952, dated Aug. 5, 2016 in English and Chineses Languages.
Pesticide Science, 1993, 38(1), (p. 1-7) "Thiazole Carboxanilide Fungicides: A New Structure-Activity Relationship for Succinate Dehydrogenase Inhibitors" W. G. Phillips & J. M. Rejda-Heath.
Bioorganic & Medicinal Chemistry. 2012, 20(3), (p. 1213-1221) "Inhibition of Dengue Virus and West Nile Virus Proteases by Click Chemistry-Derived Benz[d]isothiazol-3(2H)-One Deriyiatives" K. Tiew, D. Dou, T. Teramoto, H. Lai, K. R. Alliston, G. H. Lushington, R. Padmanabhan, W. C. Groutas.
Agrochemicals, 2007, 46(5), (p. 307-309) "Synthesis of Flumiclorac-Pentyl" Z. Li-Yong, W. Min.
Written Opinion of the International Searching Authority for International Application No. PCT/CN2016/080952, dated May 8, 2016 (11 pages in Chinese with English translation).
International Preliminary Report on Patentability for International Application No. PCT/CN2016/080952, dated Nov. 7, 2017 (13 pages in Chinese with English translation).

*Primary Examiner* — Jeffrey H Murray
(74) *Attorney, Agent, or Firm* — Smith, Gambrell & Russell, LLP

(57) ABSTRACT

The present invention belongs to the field of fungicides, and relates to an amide compound and the preparation method and use thereof. The amide compound is as shown in general formula I:

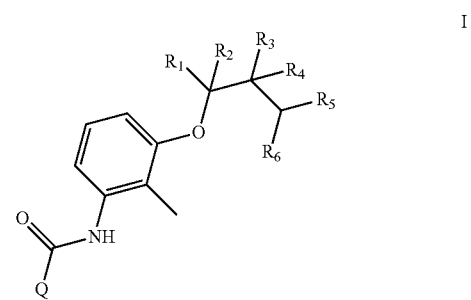

Each substituent in Formula I is defined in the description. The compound of general formula I of the present invention has an outstanding fungicidal activity, and can be used for controlling fungal diseases.

10 Claims, No Drawings

AMIDE COMPOUND AND THE PREPARATION METHOD AND USE THEREOF

FIELD OF THE INVENTION

This invention belongs to the field of fungicide, relates to one kind of amide compound and the preparation method and use thereof.

BACKGROUND OF THE INVENTION

The research for novel and improved fungicidal compounds or compositions is continually needed because of the emergence and development of the fungi resistance to the existing fungicides after a period of applications.

The fungicidal activities of pyrazole amide and thiazolamide compounds have been disclosed. For example, pyrazole amide compounds $KC_1$, $KC_2$, $KC_3$ and $KC_4$ (compounds of 3, 2, 10 and 4 in the patent) were disclosed the structures and fungicidal activity in JP62249975. JP5657776 disclosed the thiazolamide structures and fungicidal activity of $KC_5$ (compounds of 1 in the patent). *Pesticide Science*, 1993, 38(1): 1-7 disclosed the thiazolamide structures and fungicidal activity of $KC_6$ (compound of XIV in the paper).

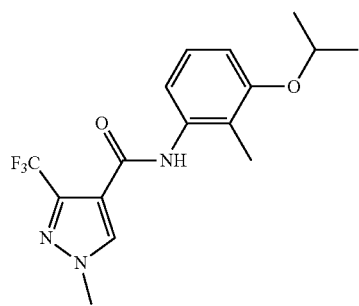

KC$_1$

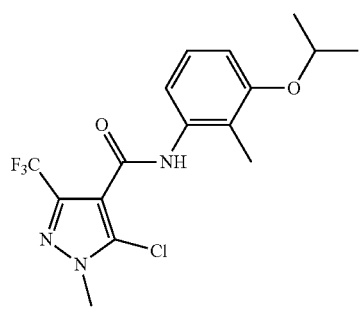

KC$_2$

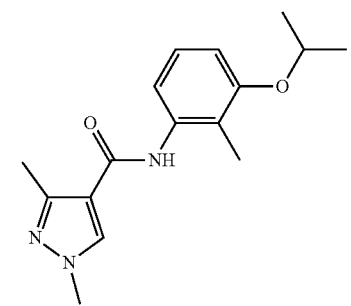

KC$_3$

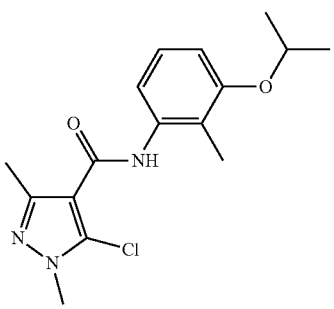

KC$_4$

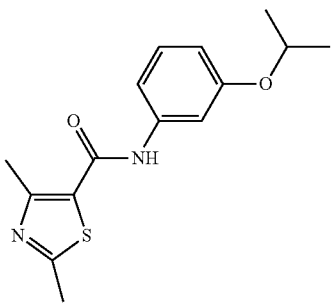

KC$_5$

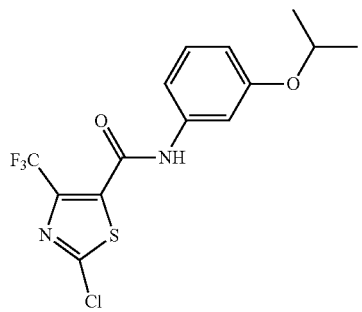

KC$_6$

There are no compounds according to the present invention are described in state of the arts.

SUMMARY OF THE INVENTION

The purpose of this invention is to provide a kind of amide compounds with better fungicidal activities, and their applications for controlling disease in agriculture or forestry.

In order to achieve the above purpose, the technical embodiments of this invention are as follows:

An amide compounds as represented by the general formula I:

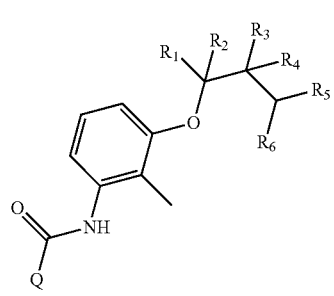

I

Wherein:

$R_1$, $R_2$, $R_3$, $R_4$, $R_5$ and $R_6$ are independently of one another represent H, halogen, CN, $C_1$-$C_{12}$ alkyl, $C_1$-$C_{12}$ alkoxy, $C_1$-$C_{12}$ haloalkyl, $C_3$-$C_6$ cycloalkyl, $C_3$-$C_6$ halocycloalkyl, $C_2$-$C_6$ alkenyl, $C_2$-$C_6$ alkynyl, hydroxyl-($C_1$-$C_6$) alkyl, ($C_1$-$C_6$) alkoxy-($C_1$-$C_6$) alkyl, ($C_3$-$C_6$) cycloalkyl-($C_1$-$C_6$) alkoxy-($C_1$-$C_6$) alkyl, ($C_1$-$C_6$) haloalkoxy-($C_1$-$C_6$) alkyl, ($C_3$-$C_8$) alkenyloxy-($C_1$-$C_6$) alkyl, ($C_3$-$C_8$) alkynyloxy-($C_1$-$C_6$) alkyl, aryl-($C_1$-$C_6$) alkoxy-($C_1$-$C_6$) alkyl, $C_1$-$C_6$ alkoxycarbonyl, $C_1$-$C_6$ haloalkoxycarbonyl, $C_3$-$C_6$ cycloalkoxycarbonyl, $C_3$-$C_6$ halocycloalkoxycarbonyl, ($C_3$-$C_6$) cycloalkyl-($C_1$-$C_6$) alkoxycarbonyl, aryloxycarbonyl, $C_1$-$C_6$ alkylaminocarbonyl, $C_3$-$C_6$ cycloalkylaminocarbonyl, ($C_3$-$C_6$) cycloalkyl-($C_1$-$C_6$) alkylaminocarbonyl, arylaminocarbonyl, aryl-($C_1$-$C_6$) alkylaminocarbonyl, and the aryl groups of the above-mentioned aryl-($C_1$-$C_6$) alkoxy-($C_1$-$C_6$) alkyl, aryloxycarbonyl, arylaminocarbonyl, aryl-($C_1$-$C_6$) alkylaminocarbonyl substituted by at most 6 (1-6) the same or different $R_7$;

Wherein aryl is benzene, 5- or 6-membered heterocyclic ring having 1 to 3 heteroatoms or a 5- or 6-membered benzoheterocyclic ring having 1 to 3 heteroatoms;

$R_7$ is halogen, nitro, CN, $C_1$-$C_6$ alkyl or $C_1$-$C_6$ haloalkyl;

Q is $Q_1$ or $Q_2$;

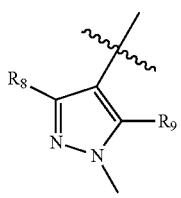

Q₁

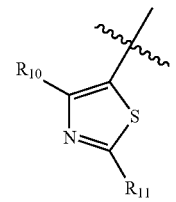

Q₂

$R_8$ is $C_1$-$C_3$ alkyl, $C_1$-$C_3$ haloalkyl or $C_3$-$C_6$ cycloalkyl;

$R_9$ is H, halogen or methyl;

$R_9$ is not H, when $R_8$ is difluoromethyl;

$R_{10}$ and $R_{11}$ are independently of one another represent $C_1$-$C_6$ alkyl, $C_1$-$C_6$ haloalkyl or $C_3$-$C_6$ cycloalkyl.

The preferred compounds of the general formula I in this invention are:

$R_1$, $R_2$, $R_3$, $R_4$, $R_5$ and $R_6$ are independently of one another represent H, halogen, CN, $C_1$-$C_{12}$ alkyl, $C_1$-$C_6$ alkoxy, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, hydroxyl-($C_1$-$C_3$) alkyl, ($C_1$-$C_3$) alkoxy-($C_1$-$C_3$) alkyl, ($C_3$-$C_6$) cycloalkyl-($C_1$-$C_3$) alkoxy-($C_1$-$C_3$) alkyl, ($C_1$-$C_3$) haloalkoxy-($C_1$-$C_3$) alkyl, ($C_3$-$C_6$) alkenyloxy-($C_1$-$C_3$) alkyl, ($C_3$-$C_6$) alkynyloxy-($C_1$-$C_6$) alkyl, aryl-($C_1$-$C_3$) alkoxy-($C_1$-$C_3$) alkyl, $C_1$-$C_3$ alkoxycarbonyl, $C_1$-$C_3$ haloalkoxycarbonyl, $C_3$-$C_6$ cycloalkoxycarbonyl, $C_3$-$C_6$ halocycloalkoxycarbonyl, ($C_3$-$C_6$) cycloalkyl-($C_1$-$C_3$) alkoxycarbonyl, aryloxycarbonyl, $C_1$-$C_3$ alkylaminocarbonyl, $C_3$-$C_6$ cycloalkylaminocarbonyl, ($C_3$-$C_6$) cycloalkyl-($C_1$-$C_3$) alkylaminocarbonyl, arylaminocarbonyl, aryl-($C_1$-$C_3$) alkylaminocarbonyl, and the aryl groups of the above-mentioned aryl-($C_1$-$C_3$) alkoxy-($C_1$-$C_3$) alkyl, aryloxycarbonyl, arylaminocarbonyl, aryl-($C_1$-$C_3$) alkylaminocarbonyl substituted by at most 6 (1-6) the same or different $R_7$;

The aryl is selected from benzene, 5- or 6-membered heterocyclic ring having 1 to 3 heteroatoms or a 5- or 6-membered benzoheterocyclic ring having 1 to 3 heteroatoms;

$R_7$ is halogen, nitro, CN, $C_1$-$C_3$ alkyl or $C_1$-$C_3$ haloalkyl;

Q is $Q_1$ or $Q_2$;

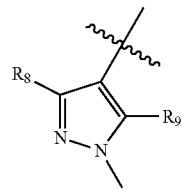

Q₁

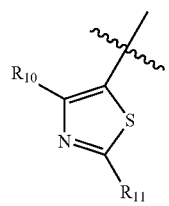

Q₂

$R_8$ is $C_1$-$C_3$ alkyl, $C_1$-$C_3$ haloalkyl or $C_3$-$C_6$ cycloalkyl;

$R_9$ is H, halogen or methyl;

$R_9$ is not H, when $R_8$ is difluoromethyl;

$R_{10}$ and $R_{11}$ are independently of one another represent $C_1$-$C_3$ alkyl, $C_1$-$C_3$ haloalkyl or $C_3$-$C_6$ cycloalkyl.

The further preferred compounds of the general formula I in this invention are:

$R_1$, $R_2$, $R_3$, $R_4$, $R_5$ and $R_6$ are independently of one another represent H, F, Cl, Br, I, CN, $C_1$-$C_{12}$ alkyl, $C_1$-$C_3$ alkoxy, $C_1$-$C_6$ haloalkyl, $C_3$-$C_6$ cycloalkyl, $C_3$-$C_6$ halocycloalkyl, $C_2$-$C_6$ alkenyl, $C_2$-$C_6$ alkynyl, hydroxyl-($C_1$-$C_3$) alkyl, ($C_1$-$C_3$) alkoxy-($C_1$-$C_3$) alkyl, ($C_3$-$C_6$) cycloalkyl-($C_1$-$C_3$) alkoxy-($C_1$-$C_3$) alkyl, ($C_1$-$C_3$) haloalkoxy-($C_1$-$C_3$) alkyl, ($C_3$-$C_6$) alkenyloxy-($C_1$-$C_3$) alkyl, ($C_3$-$C_6$) alkynyloxy-($C_1$-$C_6$) alkyl, aryl-($C_1$-$C_3$) alkoxy-($C_1$-$C_3$) alkyl, $C_1$-$C_3$ alkoxycarbonyl, $C_1$-$C_3$ haloalkoxycarbonyl, $C_3$-$C_6$ cycloalkoxycarbonyl, $C_3$-$C_6$ halocycloalkoxycarbonyl, ($C_3$-$C_6$) cycloalkyl-($C_1$-$C_3$) alkoxycarbonyl, aryloxycarbonyl, $C_1$-$C_3$ alkylaminocarbonyl, $C_3$-$C_6$ cycloalkylaminocarbonyl, ($C_3$-$C_6$) cycloalkyl-($C_1$-$C_3$) alkylaminocarbonyl, arylaminocarbonyl, aryl-($C_1$-$C_3$) alkylaminocarbonyl, and the aryl groups of the above-mentioned aryl-($C_1$-$C_3$) alkoxy-($C_1$-$C_3$) alkyl, aryloxycarbonyl, arylaminocarbonyl, aryl-($C_1$-$C_3$) alkylaminocarbonyl substituted by at most 6 (1-6) the same or different $R_7$.

Wherein aryl is benzene, furan, thiophene, pyrrole, pyrazole, oxazole, isoxazole, thiazolyl, pyridine, pyrazine, pyrimidine, pyridazine, benzoxazole, benzothiazole, quinoxaline or quinazoline;

$R_7$ is F, Cl, Br, I, nitro, CN, $C_1$-$C_3$ alkyl or $C_1$-$C_3$ haloalkyl;

Q is $Q_1$ or $Q_2$;

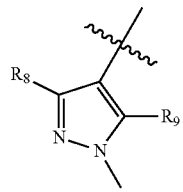

$Q_1$

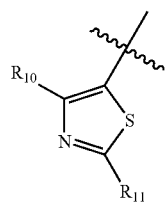

$Q_2$ $R_8$ is $C_1$-$C_3$ alkyl, $C_1$-$C_3$ haloalkyl or $C_3$-$C_6$ cycloalkyl;

$R_9$ is H, halogen or methyl;

$R_9$ is not H, when $R_8$ is difluoromethyl;

$R_{10}$ and $R_{11}$ are independently of one another represent $C_1$-$C_3$ alkyl, $C_1$-$C_3$ haloalkyl or $C_3$-$C_6$ cycloalkyl.

The further preferred compounds of the general formula I in this invention are:

$R_1$ is F, $C_1$-$C_3$ alkyl or $C_1$-$C_3$ haloalkyl;

$R_2$, $R_3$, $R_4$ and $R_5$ are independently of one another represent H, F, $C_1$-$C_3$ alkyl or $C_1$-$C_3$ haloalkyl;

$R_6$ is $C_1$-$C_{12}$ alkyl;

Q is $Q_1$ or $Q_2$;

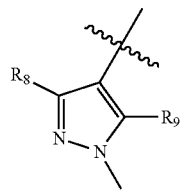

$Q_1$

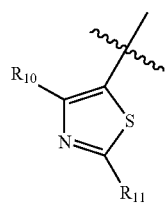

$Q_2$ $R_8$ is methyl, ethyl, n-propyl, i-propyl, trifluoromethyl, difluoromethyl, pentafluoroethyl, heptafluoroisopropyl or cyclopropyl;

$R_9$ is H, F, Cl, Br, I or methyl;

$R_9$ is not H, when $R_8$ is difluoromethyl;

$R_{10}$ and $R_{11}$ are independently of one another represent methyl, ethyl, n-propyl, i-propyl, cyclopropyl, difluoromethyl, trifluoromethyl, pentafluoroethyl, heptafluoroisopropyl.

The particularly preferred compounds of the general formula I in this invention are:

$R_1$ is $C_1$-$C_3$ alkyl;

$R_2$, $R_3$, $R_4$ and $R_5$ are independently of one another represent H;

$R_6$ is $C_1$-$C_{12}$ alkyl;

Q is $Q_1$ or $Q_2$;

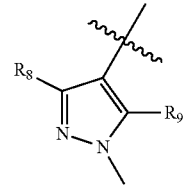

$Q_1$

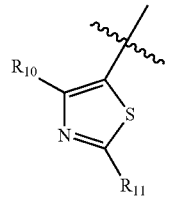

$Q_2$ $R_8$ is methyl or difluoromethyl;

$R_9$ is F or Cl;

$R_{10}$ and $R_{11}$ are independently of one another represent methyl, difluoromethyl, trifluoromethyl or cyclopropyl.

The particularly preferred compounds of the general formula I in this invention are:

$R_1$ is $C_1$-$C_3$ alkyl;

$R_2$, $R_3$, $R_4$ and $R_5$ are independently of one another represent H;

$R_6$ is $C_1$-$C_6$ alkyl;

Q is $Q_1$ or $Q_2$;

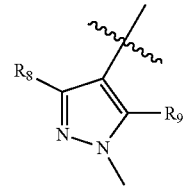

$Q_1$

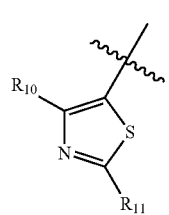

$Q_2$ $R_8$ is methyl or difluoromethyl;

$R_9$ is F or Cl;

$R_{10}$ and $R_{11}$ are independently of one another represent methyl, difluoromethyl, trifluoromethyl or cyclopropyl.

In above definitions of the compounds of general formula I, the terms used are generally defined as follows:

The term "alkyl" indicates straight-chain or branched alkyl such as methyl, ethyl, n-propyl, i-propyl, etc. "haloalkyl" indicates alkyl substituted with one or more halogen atoms such as chloroethyl, trifluoromethyl, difluoromethyl, heptafluoroisopropyl, etc. "Cycloalkyl" indicates cyclo-chain forms such as cyclopropyl, cyclobutyl, cyclopropylmethyl, methylcyclopropyl, etc. "Alkenyl" indicates straight-chain or branched alkenes such as 1-propenyl, 2-propenyl, etc. "Alkynyl" includes straight-chain or branched alkynes such as 1-propynyl, 2-propynyl, etc.

"Alkoxy" is that the end of alkyl is oxygen, such as methoxy, ethoxy, n-propyloxy, i-propyloxy, etc. "halogen" indicates F, Cl, Br, I.

The technical embodiments of this invention also contain the prepared methods of amide (the compounds of general formula I), each group of formulas are as defined above, unless otherwise specified.

Method I:

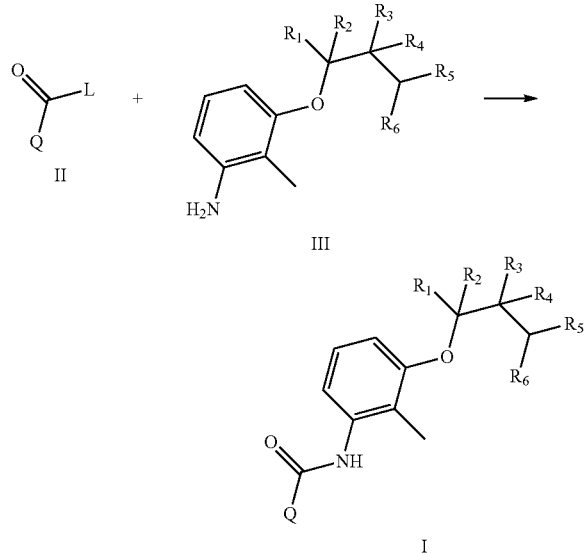

The compounds of general formula II and III are reacted in an appropriate solvent to yield the compounds of general formula I at a certain temperature from −10° C. to boiling point for 30 minutes to 48 hours.

The appropriate solvent is selected from dichloromethane, chloroform, carbon tetrachloride, hexane, benzene, toluene, ethyl acetate, acetonitrile, tetrahydrofuran, dioxane, N, N-dimethylformamide or dimethyl sulfoxide, etc.

It is advantageous to add suitable bases to the reaction, suitable bases include hydrides of alkali metal such as lithium, sodium or potassium, such as sodium hydride, hydroxide of alkali metals such as lithium, sodium or potassium, such as sodium hydroxide, may also be alkali metal carbonates such as sodium carbonate, may also be an organic base such as triethylamine, sodium tert-butoxide, etc.

When Q is selected from Q1, compounds of general formula II can be prepared according to the procedures in the CN101979375A. When Q is selected from Q2, compounds of general formula II can be prepared according to the procedures in the CN1043127A.

The compounds of general formula III can be prepared according to the procedures as in the following reference: Bioorganic & Medicinal Chemistry, 2012, 20(3): 1213-1221; Agrochemicals, 2007, 46(5):307-309.

Method II:

Wherein, L is a leaving group, X is a halogen.

The compounds of general formula II reacted with IV (commercially available) to yield the compounds of general formula V in an appropriate solvent and in the presence of suitable bases at a certain temperature from −10° C. to boiling point for 0.5 hour to 48 hours.

The appropriate solvent is selected from dichloromethane, chloroform, carbon tetrachloride, hexane, benzene, toluene, ethyl acetate, acetonitrile, tetrahydrofuran, dioxane, N, N-dimethylformamide or dimethyl sulfoxide, etc.

Suitable bases include hydrides of alkali metal such as lithium, sodium or potassium, such as sodium hydride, hydroxide of alkali metals such as lithium, sodium or potassium, such as sodium hydroxide, may also be alkali metal carbonates such as sodium carbonate, may also be an organic base such as triethylamine, sodium tert-butoxide, etc.

The compounds of general formula V reacted with VI (Commercially available) to yield the compounds of general formula I in an appropriate solvent and in the presence of suitable bases at a certain temperature from −10° C. to boiling point for 30 minutes to 48 hours.

The appropriate solvent is selected from dichloromethane, chloroform, carbon tetrachloride, hexane, benzene, toluene, ethyl acetate, acetonitrile, tetrahydrofuran, dioxane, N, N-dimethylformamide or dimethyl sulfoxide, etc.

Suitable bases include hydrides of alkali metal such as lithium, sodium or potassium, such as sodium hydride, hydroxide of alkali metals such as lithium, sodium or potassium, such as sodium hydroxide, may also be alkali metal carbonates such as sodium carbonate, may also be an organic base such as triethylamine, sodium tert-butoxide, etc.

The compounds of general formula IV are commercially available.

Typical compounds of the amide compounds of the general formula I are listed in Tables 1 to 3. The present invention can be further illustrated by the present invention, but is not intended to limit the scope of the present invention. "Me" indicates methyl, "Et" indicates ethyl, "n-Pr" indicates n-propyl, "i-Pr" indicates i-propyl, "cyc-Pr" indicates cyclopropyl, "n-Bu" indicates n-butyl.

Table 1 shows the structures and their physical properties of some representative compounds of general formula I, wherein Q is selected from $Q_1$, $R_2$, $R_3$, $R_4$, $R_5$ are selected from hydrogen.

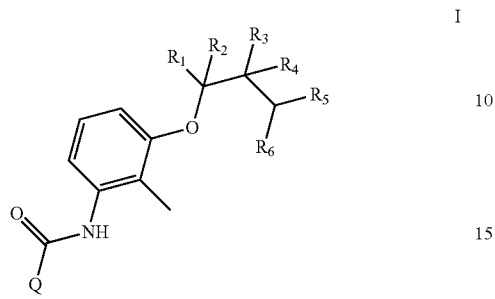

I

TABLE 1 physical properties of some representative compounds of general formula I

| No. | $R_1$ | $R_6$ | $R_8$ | $R_9$ | Appearance (m.p. (° C.)) |
|---|---|---|---|---|---|
| 1 | Me | Et | Me | H | |
| 2 | Me | Et | i-Pr | H | Yellow oil |
| 3 | Me | Et | cyc-Pr | H | |
| 4 | Me | Et | Me | Cl | White solid (121-122) |
| 5 | Me | Et | Et | Cl | Yellow solid (85-86) |
| 6 | Me | Et | i-Pr | Cl | |
| 7 | Me | Et | cyc-Pr | Cl | |
| 8 | Me | Et | Me | F | Yellow solid (54-55) |
| 9 | Me | Et | i-Pr | F | |
| 10 | Me | Et | cyc-Pr | F | |
| 11 | Me | Et | $CF_2H$ | Cl | White solid (77-78) |
| 12 | Me | Et | $CF_2H$ | F | Yellow solid (72-73) |
| 13 | Me | Et | $CF_3$ | H | Yellow oil |
| 14 | Me | Et | $CF_3$ | Cl | |
| 15 | Me | n-Pr | Me | Cl | White solid (98-99) |
| 16 | Me | n-Pr | Et | Cl | Yellow solid (65-66) |
| 17 | Me | n-Pr | Me | F | Yellow solid (77-78) |
| 18 | Me | n-Pr | $CF_2H$ | Cl | Yellow solid (75-76) |
| 19 | Me | n-Pr | $CF_2H$ | F | Yellow solid (68-69) |
| 20 | Me | n-Pr | $CF_3$ | H | |
| 21 | Me | n-Pr | $CF_3$ | Cl | |
| 22 | Me | n-Bu | Me | Cl | White solid (79-80) |
| 23 | Me | n-Bu | Et | Cl | Yellow solid (40-41) |
| 24 | Me | n-Bu | i-Pr | Cl | |
| 25 | Me | n-Bu | cyc-Pr | Cl | |
| 26 | Me | n-Bu | Me | F | Yellow solid (95-96) |
| 27 | Me | n-Bu | $CF_2H$ | Cl | Yellow solid (77-78) |
| 28 | Me | n-Bu | $CF_2H$ | F | Yellow solid (64-65) |
| 29 | Me | n-Bu | $CF_3$ | H | Yellow oil |
| 30 | Me | n-Bu | $CF_3$ | Cl | White solid (99-100) |
| 31 | Et | Et | Me | Cl | White solid (85-86) |
| 32 | Et | Et | Me | F | |
| 33 | Et | Et | $CF_2H$ | Cl | Yellow solid (83-84) |
| 34 | Et | Et | $CF_2H$ | F | Yellow solid (79-80) |
| 35 | Et | Et | $CF_3$ | H | Yellow oil |
| 36 | Et | Et | $CF_3$ | Cl | White solid (106-107) |
| 37 | 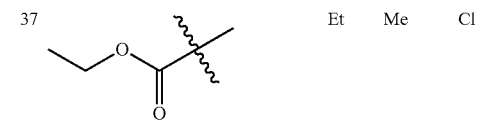 | Et | Me | Cl | |
| 38 | 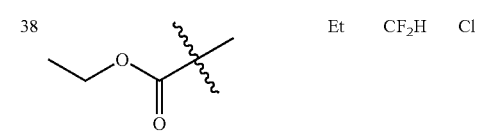 | Et | $CF_2H$ | Cl | |

TABLE 1-continued physical properties of some representative compounds of general formula I

| No. | R₁ | R₆ | R₈ | R₉ | Appearance (m.p. (° C.)) |
|---|---|---|---|---|---|
| 39 | ethyl ester group | Et | CF₂H | F | |
| 40 | ethyl ester group | n-Bu | Me | Cl | |
| 41 | ethyl ester group | n-Bu | CF₂H | Cl | Yellow solid (86-87) |
| 42 | ethyl ester group | n-Bu | CF₂H | F | Yellow solid (78-79) |
| 43 | methoxymethyl | Et | CF₂H | Cl | |
| 44 | isopropoxymethyl | Et | CF₂H | Cl | |
| 45 | allyloxymethyl | Et | CF₂H | Cl | |
| 46 | propargyloxymethyl | Et | CF₂H | Cl | |
| 47 | benzyloxymethyl | Et | CF₂H | Cl | |
| 48 | methoxyethyl | n-Bu | CF₂H | Cl | |
| 49 | isopropoxyethyl | n-Bu | CF₂H | Cl | |
| 50 | benzyloxyethyl | n-Bu | CF₂H | Cl | |

TABLE 1-continued physical properties of some representative compounds of general formula I

| No. | R$_1$ | R$_6$ | R$_8$ | R$_9$ | Appearance (m.p. (° C.)) |
|---|---|---|---|---|---|
| 51 | cyclopropylmethoxyethyl | n-Bu | CF$_2$H | Cl | |
| 52 | N-propylcarbamoyl(methyl) | Et | CF$_2$H | Cl | |
| 53 | N-benzylcarbamoyl(methyl) | Et | CF$_2$H | Cl | |
| 54 | N-phenylcarbamoyl(methyl) | Et | CF$_2$H | Cl | |
| 55 | N-propylcarbamoyl(methyl) | n-Bu | CF$_2$H | Cl | |
| 56 | N-benzylcarbamoyl(methyl) | n-Bu | CF$_2$H | Cl | |
| 57 | N-phenylcarbamoyl(methyl) | n-Bu | CF$_2$H | Cl | |
| 58 | CF$_3$ | | Et | CF$_2$H | Cl | |

Table 2 shows the structures and their physical properties of some representative compounds of general formula I, wherein Q is selected from Q$_1$, R$_2$, R$_3$ are selected from hydrogen.

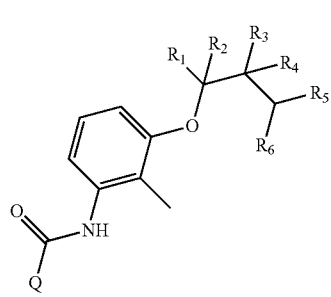

I

TABLE 2 physical properties of some representative compounds of general formula I

| No. | R$_1$ | R$_4$ | R$_5$ | R$_6$ | R$_8$ | R$_9$ | Appearance (m.p. (° C.)) |
|---|---|---|---|---|---|---|---|
| 59 | CF$_3$ | F | F | CH(CH$_3$)$_2$ with F | CF$_2$H | Cl | |
| 60 | CF$_3$ | F | F | C(CH$_3$)(F)(CF$_3$) | CF$_2$H | Cl | |

TABLE 2-continued physical properties of some representative compounds of general formula I

| No. | $R_1$ | $R_4$ | $R_5$ | $R_6$ | $R_8$ | $R_9$ | Appearance (m.p. (° C.)) |
|---|---|---|---|---|---|---|---|
| 61 | $CF_3$ | $CF_3$ | $CF_3$ | ⟨CF_3/CF_3⟩ | $CF_2H$ | Cl | |
| 62 | Me | H | CN | Et | $CF_2H$ | Cl | |
| 63 | Me | Me | H | Et | $CF_2H$ | Cl | |
| 64 | Me | Me | CN | Et | $CF_2H$ | Cl | |
| 65 | cyc-Pr | H | H | Et | $CF_2H$ | Cl | |

Table 3 shows the structures and their physical properties of some representative compounds of general formula I, wherein Q is selected from $Q_2$, $R_2$, $R_3$, $R_4$, $R_5$ are selected from hydrogen.

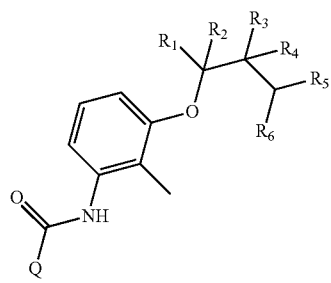

I

TABLE 3 physical properties of some representative compounds of general formula I

| No. | $R_1$ | $R_6$ | $R_{10}$ | $R_{11}$ | Appearance (m.p. (° C.)) |
|---|---|---|---|---|---|
| 66 | Me | Et | Me | Me | Yellow oil |
| 67 | Me | Et | Et | Me | Yellow oil |
| 68 | Me | Et | i-Pr | Me | |
| 69 | Me | Et | cyc-Pr | Me | |
| 70 | Me | Et | Me | $CF_3$ | Yellow solid (70-71) |
| 71 | Me | Et | $CF_3$ | Me | Yellow oil |
| 72 | Me | Et | $CF_3$ | Et | |
| 73 | Me | Et | $CF_3$ | i-Pr | |
| 74 | Me | Et | $CF_3$ | n-Pr | |
| 75 | Me | Et | $CF_3$ | $CF_3$ | |
| 76 | Me | Et | $CF_3$ | $CF_2H$ | |
| 77 | Me | Et | $CF_2H$ | Me | Yellow oil |
| 78 | Me | Et | $CF_2H$ | $CF_3$ | |
| 79 | Me | Et | $CF_2H$ | $CF_2H$ | |
| 80 | Me | n-Pr | Me | Me | |
| 81 | Me | n-Pr | Et | Me | |
| 82 | Me | n-Pr | i-Pr | Me | |
| 83 | Me | n-Pr | cyc-Pr | Me | |
| 84 | Me | n-Pr | Me | $CF_3$ | Yellow oil |
| 85 | Me | n-Pr | $CF_3$ | Me | Yellow oil |
| 86 | Me | n-Pr | $CF_3$ | Et | |
| 87 | Me | n-Pr | $CF_3$ | i-Pr | |
| 88 | Me | n-Pr | $CF_3$ | n-Pr | |
| 89 | Me | n-Pr | $CF_3$ | $CF_3$ | |
| 90 | Me | n-Pr | $CF_3$ | $CF_2H$ | |
| 91 | Me | n-Pr | $CF_2H$ | Me | |
| 92 | Me | n-Pr | $CF_2H$ | $CF_2H$ | |
| 93 | Me | n-Bu | Me | Me | |

TABLE 3-continued physical properties of some representative compounds of general formula I

| No. | $R_1$ | $R_6$ | $R_{10}$ | $R_{11}$ | Appearance (m.p. (° C.)) |
|---|---|---|---|---|---|
| 94 | Me | n-Bu | $CF_3$ | Me | White solid (65-67) |
| 95 | Me | n-Bu | $CF_3$ | Et | |
| 96 | Me | n-Bu | $CF_3$ | i-Pr | |
| 97 | Me | n-Bu | $CF_3$ | n-Pr | |
| 98 | Me | n-Bu | $CF_3$ | $CF_3$ | |
| 99 | Me | n-Bu | $CF_3$ | $CF_2H$ | |
| 100 | Me | n-Bu | $CF_2H$ | Me | Red oil |
| 101 | Me | H | Me | Me | |
| 102 | Me | H | $CF_3$ | Me | Yellow solid (95-96) |
| 103 | Me | H | $CF_3$ | Et | |
| 104 | Me | H | $CF_3$ | i-Pr | |
| 105 | Me | H | $CF_3$ | n-Pr | |
| 106 | Me | H | $CF_3$ | $CF_3$ | |
| 107 | Me | H | $CF_3$ | $CF_2H$ | |
| 108 | Me | H | $CF_2H$ | Me | |
| 109 | Me | Me | Me | Me | Yellow oil |
| 110 | Me | Me | Et | Me | Yellow oil |
| 111 | Me | Me | Et | $CF_3$ | Yellow oil |
| 112 | Me | Me | $CF_3$ | Me | Yellow solid (70-71) |
| 113 | Me | Me | $CF_3$ | Et | |
| 114 | Me | Me | $CF_3$ | i-Pr | |
| 115 | Me | Me | $CF_3$ | n-Pr | |
| 116 | Me | Me | $CF_3$ | $CF_3$ | |
| 117 | Me | Me | $CF_3$ | $CF_2H$ | |
| 118 | Me | Me | $CF_2H$ | Me | |

$^1$H NMR (300 MHz, CDCl$_3$) data of representative compounds:

Compound 2: 7.70 (s, 1H), 7.47 (d, 1H), 7.15-7.18 (m, 2H), 6.70 (d, 1H), 4.35-4.38 (m, 1H), 3.89 (s, 3H), 3.45-3.55 (m, 1H), 2.16 (s, 3H), 1.56-1.75 (m, 2H), 1.28-1.46 (m, 13H), 0.88-0.96 (m, 3H).

Compound 4: 7.72 (s, 1H), 7.59 (d, 1H), 7.17 (t, 1H), 6.71 (d, 1H), 4.33-4.40 (m, 1H), 3.84 (s, 3H), 2.52 (s, 3H), 2.19 (s, 3H), 1.57-1.80 (m, 2H), 1.26-1.47 (m, 7H), 0.88-0.97 (m, 3H).

Compound 5: 7.73 (s, 1H), 7.58 (d, 1H), 7.16 (t, 1H), 6.71 (d, 1H), 4.30~4.40 (m, 1H), 3.86 (s, 3H), 2.96 (q, 2H), 2.20 (s, 3H), 1.25~1.80 (m, 6H), 1.29 (d, 3H), 1.28 (t, 3H), 0.91 (t, 3H).

Compound 8: 7.58 (d, 1H), 7.32~7.33 (m, 1H), 7.15 (t, 1H), 6.70 (d, 1H), 4.30~4.40 (m, 1H), 3.74 (s, 3H), 2.49 (s, 3H), 2.16 (s, 3H), 1.23~2.05 (m, 6H), 1.27 (d, 3H), 0.91 (t, 3H).

Compound 11: 7.89 (s, 1H), 7.58 (d, 1H), 7.21 (t, 1H), 7.19 (t, 1H), 6.76 (d, 1H), 4.38-4.42 (m, 1H), 3.99 (s, 3H), 2.22 (s, 3H), 1.60-1.80 (m, 2H), 1.32-1.47 (m, 7H), 0.94-1.00 (m, 3H).

Compound 12: 7.58 (s, 1H), 7.52 (d, 1H), 7.15 (t, 1H), 7.05 (t, 1H), 6.72 (d, 1H), 4.15~4.21 (m, 1H), 3.85 (s, 3H), 2.16 (s, 3H), 1.50~1.80 (m, 2H), 1.27~1.50 (m, 4H), 1.28 (d, 3H), 0.93 (t, 3H).

Compound 13: 8.02 (s, 1H), 7.61 (s, 1H), 7.45 (d, 1H), 7.15 (t, 1H), 6.73 (d, 1H), 4.31-4.36 (m, 1H), 3.97 (s, 3H), 2.15 (s, 3H), 1.56-1.75 (m, 2H), 1.28-1.44 (m, 7H), 0.91-0.94 (m, 3H).

Compound 15: 7.72 (s, 1H), 7.59 (d, 1H), 7.16 (t, 1H), 6.70 (d, 1H), 4.32-4.36 (m, 1H), 3.85 (s, 3H), 2.52 (s, 3H), 2.19 (s, 3H), 1.65-1.79 (m, 2H), 1.27-1.58 (m, 9H), 0.86-0.94 (m, 3H).

Compound 16: 7.73 (s, 1H), 7.58 (d, 1H), 7.16 (t, 1H), 6.71 (d, 1H), 4.30~4.40 (m, 1H), 3.86 (s, 3H), 2.96 (q, 2H), 2.20 (s, 3H), 1.25~1.80 (m, 8H), 1.29 (d, 3H), 1.28 (t, 3H), 0.89 (t, 3H).

Compound 17: 7.59 (d, 1H), 7.31~7.33 (m, 1H), 7.15 (t, 1H), 6.70 (d, 1H), 4.30~4.40 (m, 1H), 3.75 (s, 3H), 2.49 (s, 3H), 2.16 (s, 3H), 1.27~1.80 (m, 8H), 1.28 (d, 3H), 0.89 (t, 3H).

Compound 18: 7.87 (s, 1H), 7.54 (d, 1H), 7.15 (t, 1H), 7.12~1.17 (m, 1H), 6.72 (d, 1H), 4.32~4.38 (m, 1H), 3.93 (s, 3H), 2.18 (s, 3H), 1.32 (d, 3H), 1.23~2.03 (m, 8H), 0.89 (t, 3H).

Compound 19: 7.58 (s, 1H), 7.52 (d, 1H), 7.14 (t, 1H), 7.05 (t, 1H), 6.72 (d, 1H), 4.32~4.38 (m, 1H), 3.83 (s, 3H), 2.18 (s, 3H), 1.31~1.76 (m, 8H), 1.28 (d, 3H), 0.89 (t, 3H).

Compound 22: 7.73 (s, 1H), 7.60 (d, 1H), 7.16 (t, 1H), 6.71 (d, 1H), 4.32-4.36 (m, 1H), 3.85 (s, 3H), 2.52 (s, 3H), 2.20 (s, 3H), 1.60-1.74 (m, 2H), 1.27-1.61 (m, 11H), 0.86-0.94 (m, 3H).

Compound 23: 7.72 (s, 1H), 7.58 (d, 1H), 7.16 (t, 1H), 6.71 (d, 1H), 4.30~4.40 (m, 1H), 3.86 (s, 3H), 2.96 (q, 2H), 2.20 (s, 3H), 1.25~1.80 (m, 10H), 1.29 (d, 3H), 1.28 (t, 3H), 0.88 (t, 3H).

Compound 26: 7.58 (d, 1H), 7.31~7.33 (m, 1H), 7.15 (t, 1H), 6.70 (d, 1H), 4.30~4.40 (m, 1H), 3.74 (s, 3H), 2.49 (s, 3H), 2.16 (s, 3H), 1.27~1.80 (m, 10H), 1.28 (d, 3H), 0.88 (t, 3H).

Compound 27: 7.87 (s, 1H), 7.55 (d, 1H), 7.16 (t, 1H), 7.13~7.18 (s, 1H), 6.73 (d, 1H), 4.32~4.38 (m, 1H), 3.94 (s, 3H), 2.19 (s, 3H), 1.29 (d, 3H), 1.23~1.80 (m, 10H), 0.90 (t, 3H).

Compound 28: 7.57 (s, 1H), 7.53 (d, 1H), 7.15 (t, 1H), 7.05 (t, 1H), 6.72 (d, 1H), 4.34~4.36 (m, 1H), 3.85 (s, 3H), 2.16 (s, 3H), 1.28 (d, 3H), 1.23~1.60 (m, 10H), 0.88 (t, 3H).

Compound 29: 8.04 (s, 1H), 7.58 (s, 1H), 7.46 (d, 1H), 7.17 (t, 1H), 6.73 (d, 1H), 4.32-4.36 (m, 1H), 3.99 (s, 3H), 2.15 (s, 3H), 1.65-1.79 (m, 2H), 1.23-1.61 (m, 11H), 0.86-0.90 (m, 3H).

Compound 30: 7.53-7.56 (m, 2H), 7.17 (t, 1H), 6.73 (d, 1H), 4.32-4.36 (m, 1H), 3.96 (s, 3H), 2.16 (s, 3H), 1.65-1.79 (m, 2H), 1.27-1.58 (m, 11H), 0.86-0.90 (m, 3H).

Compound 31: 7.73 (s, 1H), 7.58 (d, 1H), 7.15 (t, 1H), 6.69 (d, 1H), 4.17-4.21 (m, 1H), 3.85 (s, 3H), 2.46 (s, 3H), 2.21 (s, 3H), 1.63-1.70 (m, 4H), 1.28-1.36 (m, 4H), 0.87-0.97 (m, 6H).

Compound 33: 7.87 (s, 1H), 7.53 (d, 1H), 7.15 (t, 1H), 7.13~7.18 (s, 1H), 6.71 (d, 1H), 4.18~4.21 (m, 1H), 3.94 (s, 3H), 2.19 (s, 3H), 1.61~2.04 (m, 4H), 1.26~4.42 (m, 4H), 0.95 (t, 3H), 0.90 (t, 3H).

Compound 34: 7.59 (s, 1H), 7.50 (d, 1H), 7.14 (t, 1H), 7.05 (t, 1H), 6.70 (d, 1H), 4.18~4.20 (m, 1H), 3.83 (s, 3H), 2.19 (s, 3H), 1.64~4.70 (m, 4H), 1.27~1.38 (m, 4H), 0.95 (t, 3H), 0.90 (t, 3H).

Compound 35: 8.04 (s, 1H), 7.58 (s, 1H), 7.46 (d, 1H), 7.15 (t, 1H), 6.71 (d, 1H), 4.17-4.21 (m, 1H), 3.99 (s, 3H), 2.16 (s, 3H), 1.63-1.70 (m, 4H), 1.26-1.38 (m, 4H), 0.87-0.97 (m, 6H).

Compound 36: 7.54-7.61 (m, 2H), 7.15 (t, 1H), 6.71 (d, 1H), 4.17-4.21 (m, 1H), 3.96 (s, 3H), 2.17 (s, 3H), 1.63-1.72 (m, 4H), 1.28-1.41 (m, 4H), 0.83-0.97 (m, 6H).

Compound 41: 7.89 (s, 1H), 7.59 (d, 1H), 7.10 (t, 1H), 7.08-7.13 (m, 1H), 6.54 (d, 1H), 4.58~4.62 (m, 1H), 4.18 (q, 2H), 3.91 (s, 3H), 2.25 (s, 3H), 1.93~1.98 (m, 2H), 1.47~1.54 (m, 2H), 1.23 (t, 3H), 1.21~1.37 (m, 6H), 0.87 (t, 3H).

Compound 42: 7.60 (s, 1H), 7.58 (d, 1H), 7.11 (t, 1H), 7.03 (t, 1H), 6.54 (d, 1H), 4.58~4.60 (m, 1H), 4.19 (q, 2H), 3.83 (s, 3H), 2.25 (s, 3H), 1.93·2.03 (m, 2H), 1.47~4.54 (m, 2H), 1.24 (t, 3H), 1.21~1.37 (m, 6H), 0.88 (t, 3H).

Compound 66: 7.44 (d, 1H), 7.28 (s, 1H), 7.13-7.18 (t, 1H), 6.73 (d, 1H), 4.32-4.36 (m, 1H), 2.72 (s, 3H), 2.70 (s, 3H), 2.15 (s, 3H), 1.57-1.79 (m, 2H), 1.21-1.48 (m, 7H), 0.88-0.97 (m, 3H).

Compound 67: 7.46 (d, 1H), 7.25 (s, 1H), 7.13-7.18 (t, 1H), 6.72 (d, 1H), 4.32-4.36 (m, 1H), 3.07-3.14 (m, 2H), 2.72 (s, 3H), 2.15 (s, 3H), 1.55-1.79 (m, 2H), 1.21-1.47 (m, 10H), 0.88-0.96 (m, 3H).

Compound 70: 7.38-7.41 (m, 2H), 7.16-7.20 (t, 1H), 6.77 (d, 1H), 4.33-4.41 (m, 1H), 2.82 (s, 3H), 2.18 (s, 3H), 1.58-1.76 (m, 2H), 1.29-1.42 (m, 7H), 0.90-0.97 (m, 3H).

Compound 71: 7.66 (s, 1H), 7.43 (d, 1H), 7.14-7.17 (t, 1H), 6.76 (d, 1H), 4.35-4.37 (m, 1H), 2.76 (s, 3H), 2.15 (s, 3H), 1.60-1.76 (m, 2H), 1.29-1.44 (m, 7H), 0.91-0.94 (m, 3H).

Compound 77: 7.76 (s, 1H), 7.38 (d, 1H), 7.20 (t, 1H), 7.13-7.18 (t, 1H), 6.75 (d, 1H), 4.32-4.36 (m, 1H), 2.76 (s, 3H), 2.15 (s, 3H), 1.57-1.79 (m, 2H), 1.21-1.48 (m, 7H), 0.88-0.97 (m, 3H).

Compound 84: 7.44 (s, 1H), 7.39 (d, 1H), 7.16-7.20 (t, 1H), 6.77 (d, 1H), 4.33-4.41 (m, 1H), 2.82 (s, 3H), 2.17 (s, 3H), 1.61-1.79 (m, 2H), 1.21-1.42 (m, 9H), 0.87-0.95 (m, 3H).

Compound 85: 7.63 (s, 1H), 7.44 (d, 1H), 7.14-7.18 (t, 1H), 6.76 (d, 1H), 4.32-4.36 (m, 1H), 2.76 (s, 3H), 2.15 (s, 3H), 1.69-1.79 (m, 2H), 1.21-1.48 (m, 9H), 0.86-0.91 (m, 3H).

Compound 94: 7.74 (s, 1H), 7.41 (d, 1H), 7.02-7.38 (t, 1H), 7.14-7.17 (d, 1H), 6.74-6.77 (d, 1H), 4.33-4.37 (m, 1H), 2.77 (s, 3H), 2.16 (s, 3H), 1.73-1.81 (m, 2H), 1.31-1.45 (m, 8H), 1.28-1.30 (d, 3H), 0.86-0.92 (m, 3H).

Compound 100: 7.65 (s, 1H), 7.44 (d, 1H), 7.16-7.20 (t, 1H), 6.75-6.77 (d, 1H), 4.35-4.37 (m, 1H), 2.76 (s, 3H), 2.15 (s, 3H), 1.43-1.62 (m, 4H), 1.31-1.42 (m, 6H), 1.28-1.30 (d, 3H), 0.86-0.91 (m, 3H).

Compound 102: 7.63 (s, 1H), 7.44-7.47 (d, 1H), 7.14-7.20 (t, 1H), 6.75-6.77 (d, 1H), 4.28-4.34 (m, 1H), 2.77 (s, 3H), 2.16 (s, 3H), 1.62-1.81 (m, 2H), 1.28-1.30 (d, 3H), 0.96-1.01 (t, 3H), 0.86-0.91 (m, 3H).

Compound 109: 7.42-7.44 (d, 1H), 7.29 (s, 1H), 7.13-7.18 (t, 1H), 6.72-6.75 (d, 1H), 4.36-4.38 (m, 1H), 2.70 (s, 3H), 2.73 (s, 3H), 2.16 (s, 3H), 1.40-1.74 (m, 4H), 1.26-1.28 (d, 3H), 0.92-0.96 (t, 3H), 0.86-0.91 (t, 3H).

Compound 110: 7.45-7.48 (d, 1H), 7.25 (s, 1H), 7.16-7.18 (t, 1H), 6.72-6.74 (d, 1H), 4.38-4.40 (m, 1H), 3.01-3.12 (q, 2H), 2.72 (s, 3H), 2.16 (s, 3H), 1.43-1.72 (m, 4H), 1.28-1.36 (m, 6H), 0.94-0.96 (m, 3H).

Compound 111: 7.42 (s, 1H), 7.37-7.40 (d, 1H), 7.15-7.20 (t, 1H), 6.76-6.79 (d, 1H), 4.38-4.40 (m, 1H), 3.12-3.20 (q, 2H), 2.17 (s, 3H), 1.44-1.77 (m, 4H), 1.37-1.42 (t, 3H), 1.31-1.35 (d, 3H), 0.92-0.97 (t, 3H).

Compound 112: 7.63 (s, 1H), 7.44-7.46 (d, 1H), 7.17-7.20 (t, 1H), 6.76-6.78 (d, 1H), 4.37-4.39 (m, 1H), 2.76 (s, 3H), 2.15 (s, 3H), 1.40-1.73 (m, 4H), 1.30-1.39 (d, 3H), 0.92-0.97 (t, 3H).

The pyrazole amide compounds in this invention possess surprisingly high fungicidal activity compared with the known pyrazole amide compounds. So, this invention also provides the use of general formula I compounds for combatting diseases, which can control the disease of oomycetes, ascomycetes, basidiomycetes, deuteromycetes, plasmodiophoromycetes, chytridiomycetes, zygomycetes.

Some fungal diseases which under the class names listed above may be mentioned as example, but not by way of limitation.

Wheat rust, rice sheath blight, wheat sheath blight, cucumber downy mildew, grape downy mildew, wheat powdery mildew, tomato early blight, cucumber anthracnose, rice blast, wheat scab, wheat root rot, watermelon gummy stem blight, scab peanuts, peanut black spot, scab of citrus, tomato late blight, pepper root rot, cotton *verticillium* wilt, rape blackleg, take-all of wheat, banana leaf spot, wheat scab, pear scab, corn curvalaria leaf spot, cotton *fusarium* wilt disease, *ginseng* rust rot, corn leaf blight, stem rot disease of mango, cucumber blight, apple ring rot, apple valsa canker, rape sclertiniose, black leaf streak of banana, glume blight of wheat.

Another embodiment of this invention includes the fungicidal compositions, in which the compounds of general formula I are active ingredients. The weight percentage of active ingredient(s) in the compositions is from 1% to 99%. There are also acceptable carriers in agriculture in these compositions.

The compositions of the present invention can be used in the form of various formulations. Usually, amide (the compounds of general formula I) as the active ingredient can be dissolved in or dispersed to carriers or made to a formulation. So that they can be easily dispersed as a fungicide, such as a wettable powder or an emulsifiable concentrate, etc. Therefore, in these compositions, at least a liquid or solid carrier is added, and usually suitable surfactant(s) can be added when needed.

Also provided by this invention are the application methods of controlling diseases, which is to apply the compositions of the present invention to the growing loci of the fungi as above mentioned. The suitably effective dosage of the compounds of the present invention is usually within a range of from 10 g/ha to 1000 g/ha.

For some applications, one or more other fungicides, insecticides, herbicides, plant growth regulators or fertilizer can be added into the fungicidal compositions of the present invention to make additional merits and effects.

DESCRIPTION OF THE INVENTION IN DETAIL

The following synthesis examples and bioassay examples are used to further illustrate the present invention, but not to limit it.

SYNTHESIS EXAMPLES

Example 1: Synthesis of Compound 28

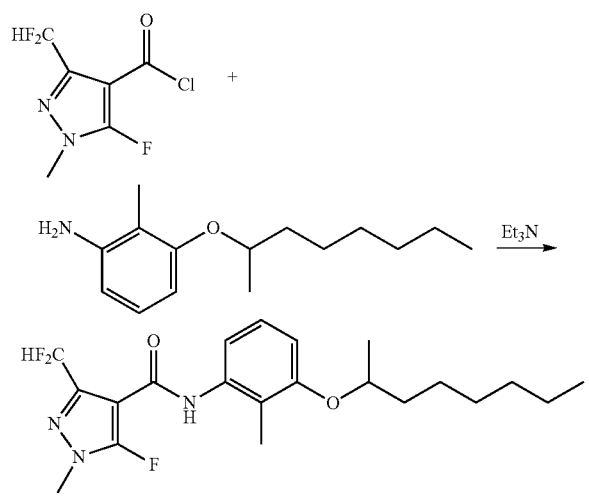

2-methyl-3-(octan-2-yloxy)aniline (240 mg, 1.03 mmol), triethylamine (110 mg, 1.09 mmol) and dichloromethane (10 mL) were added to a flask, stirred at room temperature, then the solution of 3-(difluoromethyl)-5-fluoro-1-methyl-1H-pyrazole-4-carbonyl chloride (210 mg, 0.99 mmol) in dichloromethane (10 mL) was added dropwise. After being stirred for 3 hours at room temperature, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent:ethyl acetate/petroleum ether=1/2) to give the compound 28 (250 mg) in 60.8% yield.

Example 2: Synthesis of Compound 41

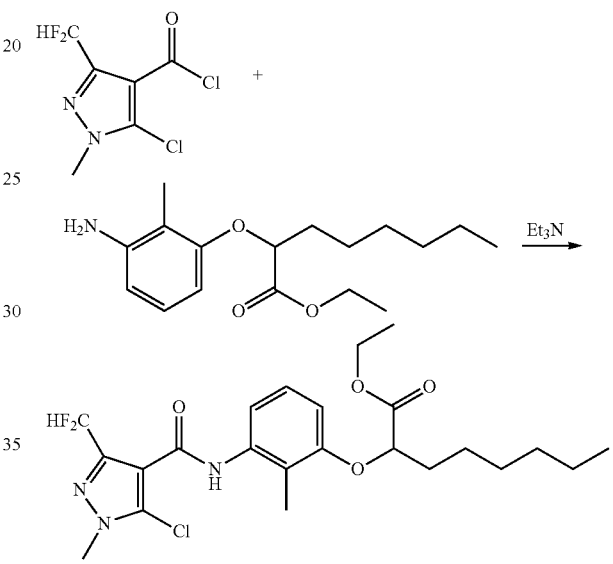

ethyl 2-(3-amino-2-methylphenoxy)octanoate (290 mg, 0.99 mmol), triethylamine (110 mg, 1.09 mmol) and dichloromethane (10 mL) were added to a flask, stirred at room temperature, then the solution of 5-chloro-3-(difluoromethyl)-1-methyl-1H-pyrazole-4-carbonyl chloride (230 mg, 1.00 mmol) in dichloromethane (10 mL) was added dropwise. After being stirred for 3 hours at room temperature, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent:ethyl acetate/petroleum ether=1/2) to give the compound 41 (190 mg) in 72.0% yield.

Example 3: Synthesis of Compound 70

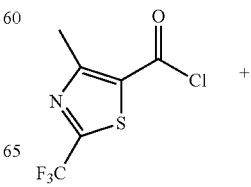

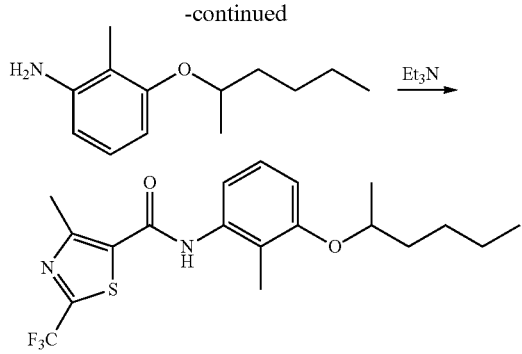

3-(hexan-2-yloxy)-2-methylaniline (230 mg, 1.10 mmol), triethylamine (140 mg, 1.33 mmol) and dichloromethane (10 mL) were added to a flask, stirred at room temperature, then the solution of 4-methyl-2-(trifluoromethyl)thiazole-5-carbonyl chloride (310 mg, 1.33 mmol) in dichloromethane (10 mL) was added dropwise. After being stirred for 3 hours at room temperature, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent:ethyl acetate/petroleum ether=1/8) to give the compound 70 (150 mg) in 33.4% yield.

Example 4: Synthesis of Compound 71

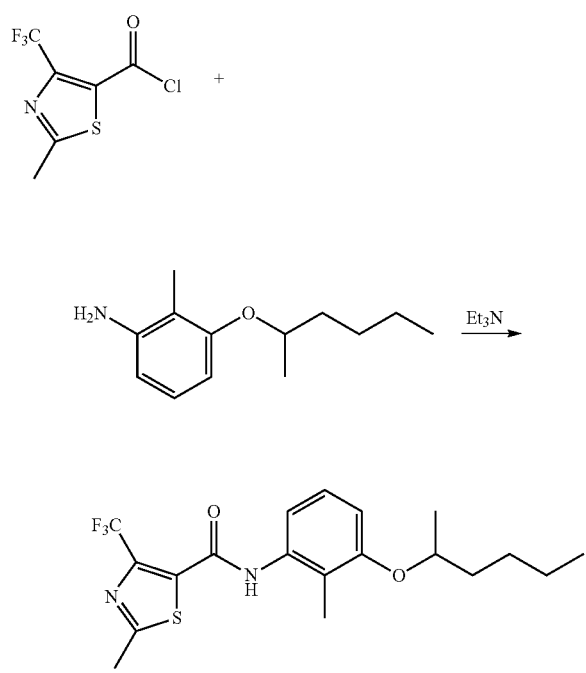

3-(hexan-2-yloxy)-2-methylaniline (200 mg, 0.96 mmol), triethylamine (120 mg, 1.17 mmol) and dichloromethane (10 mL) were added to a flask, stirred at room temperature, then the solution of 2-methyl-4-(trifluoromethyl)thiazole-5-carbonyl chloride (270 mg, 1.17 mmol) in dichloromethane (10 mL) was added dropwise. After being stirred for 3 hours at room temperature, water (30 mL) was added. The organic layer was successively washed with saturated sodium bicarbonate solution and saturated brine, dried over anhydrous magnesium sulfate and concentrated by rotary evaporator. The residue was purified by silica gel column chromatography (Fluent:ethyl acetate/petroleum ether=1/5) to give the compound 71 (250 mg) in 57.0% yield.

The compounds of general formula I in the present invention can be prepared by the above-described methods.

BIOLOGICAL EXAMPLES

Example 3 Determination of Fungicidal Activity

Fungicidal activity of the compounds in the present invention against many kinds diseases were carried out. The procedure of fungicidal activity determination is as follows:

The fungicidal activity was tested in vivo manner on the potted plants. The test compounds of the present invention were dissolved in proper solvent (choosing the solvent according their dissolving ability to the compounds, the solvents could be acetone, methanol or N,N-dimethylformide, etc. The volume ratio between solvent and liquid sprayed was equal to or less than 0.05) and dilute with water contain 0.1% Tween 80 to given concentrations. Compounds of present invention was sprayed onto the leaves of seedling according to the designed concentration. Meanwhile, water was set as the blank control, three replicates were set for each treatment, the spore suspension were inoculated on the second day after treatment, then the plants were placed in an artificial climate chamber (temperature: day 25° C., night 20° C., relative humidity 95 to 100%). 24 hours later, the plants were moved to green house to cultivated. The plants which not need to control humidity was inoculated spore suspension in green house and cultivated in green house directly. The results were investigated after the plants were fully infected relative to the blank control (usually one week). The test resluts grading 100-0 refers to the <A Manual of Assessment Keys for Plant Diseases> which edited by American Phytopathological Society. "100" refer to no infection and "0" refer to the most serious infection Some test results were listed as follows:

Protective effect against cucumber anthracnose (*Colletotrichum orbiculare*):

According the test method described above, the following compound among the test compounds exhibit good fungicidal activity against cucumber anthracnose at 400 ppm, the protective effect was 80% or more: compound 4.

Protective effect against cucumber downy mildew (*Pseudoperonospora cubensis* (Berk. et Curt.) Rostov)

According the test method described above, the following compounds among the test compounds exhibit good fungicidal activity against cucumber anthracnose at 400 ppm, the protective effect was 80% or more: compound 2, 4, 11, 13, 36, 70, 71, 102, 110 and 111.

According the test method described above, parallel test were carried out between compounds 2, 4, 11, 13, 71 and 111 of present invention and the known compounds $KC_1$, $KC_2$, $KC_3$, $KC_4$, $KC_5$ and $KC_6$ (The compounds were self-made and the structure was confirmed by $^1H$ NMR consistent with the description of the procedures). The test results are listed in table 2.

TABLE 2

The parallel protectant activity test result against cucumber downy mildew between compounds 2 and 11 of present invention and the known compounds

| Compound | Structure | 400 ppm |
|---|---|---|
| 2 | | 100 |
| 4 | | 100 |
| 11 | | 85 |
| 13 | | 100 |
| 71 | | 100 |
| 111 | | 100 |
| KC$_1$ | | 0 |

TABLE 2-continued

The parallel protectant activity test result against cucumber downy mildew between compounds 2 and 11 of present invention and the known compounds

| Compound | Structure | 400 ppm |
|---|---|---|
| KC₂ | (structure: 1-methyl-3-trifluoromethyl-5-chloro-pyrazole-4-carboxamide with N-(2-methyl-3-isopropoxyphenyl)) | 0 |
| KC₃ | (structure: 1,3-dimethyl-pyrazole-4-carboxamide with N-(2-methyl-3-isopropoxyphenyl)) | 0 |
| KC₄ | (structure: 1,3-dimethyl-5-chloro-pyrazole-4-carboxamide with N-(2-methyl-3-isopropoxyphenyl)) | 0 |
| KC₅ | (structure: 2,4-dimethyl-thiazole-5-carboxamide with N-(3-isopropoxyphenyl)) | 0 |
| KC₆ | (structure: 2-chloro-4-trifluoromethyl-thiazole-5-carboxamide with N-(2-methyl-3-isopropoxyphenyl)) | 0 |

Protective Effect Against Corn Rust (*Puccinia sorghi* Schw.):

According the test method described above, the following compounds among the test compounds exhibit good fungicidal activity against corn rust at 400 ppm, the protective effect was 80% or more: 2, 4, 11, 13, 71, 72, 102, 109, 110, 111 and 112.

According the test method described above, parallel test were carried out between compound 13 of present invention and the known compound KC₁. The test results are listed in table 3.

TABLE 3

The parallel test of protectant activity against corn rust between some compounds of present invention and the known compounds

| Compounds | Structure | 400 ppm | 6.25 ppm |
|---|---|---|---|
| 13 | (structure: 1-methyl-3-trifluoromethyl-pyrazole-4-carboxamide with N-(2-methyl-3-(pentan-2-yloxy)phenyl)) | 100 | 100 |

TABLE 3-continued

The parallel test of protectant activity against corn rust between some compounds of present invention and the known compounds

| Compounds | Structure | 400 ppm | 6.25 ppm |
|---|---|---|---|
| KC$_1$ | 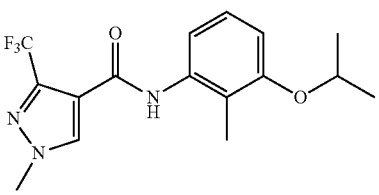 | 100 | 50 |

According the test method described above, parallel test were carried out between compound 11 of present invention and the known compound KC$_2$. The test results are listed in table 4.

TABLE 4

The parallel test of protectant activity against corn rust between some compounds of present invention and the known compounds

| Compounds | Structure | 6.25 ppm | 1.5625 ppm | 0.39 ppm |
|---|---|---|---|---|
| 11 | 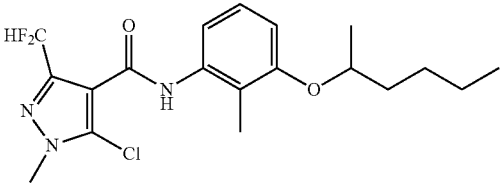 | 100 | 100 | 100 |
| KC$_2$ | 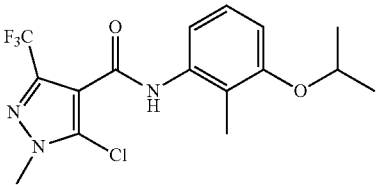 [SMILES: Cc1c(NC(=O)c2c(C(F)(F)F)nn(C)c2Cl)cccc1OC(C)C] | 100 | 65 | 0 |

According the test method described above, parallel test were carried out between compound 71 of present invention and the known compounds KC$_5$ and KC$_6$. The test results are listed in table 5.

TABLE 5

The parallel test of protectant activity against corn rust between some compounds of present invention and the known compounds

| Compounds | Structure | 400 ppm | 6.25 ppm | 1.56 ppm |
|---|---|---|---|---|
| 71 | 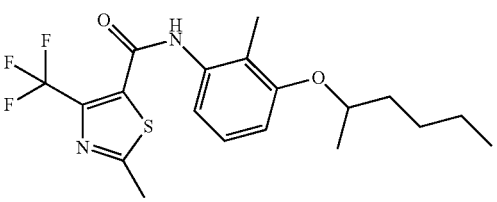 [SMILES: CCCCC(C)Oc1cccc(NC(=O)c2sc(C)nc2C(F)(F)F)c1C] | 100 | 100 | 100 |

TABLE 5-continued

The parallel test of protectant activity against corn rust between some compounds of present invention and the known compounds

| Compounds | Structure | 400 ppm | 6.25 ppm | 1.56 ppm |
|---|---|---|---|---|
| KC$_1$ | 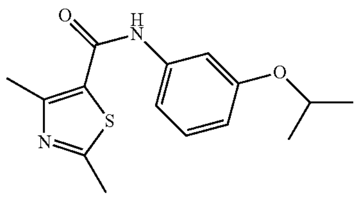 [SMILES: Cc1nc(C)c(C(=O)Nc2cccc(OC(C)C)c2)s1] | 100 | 95 | 20 |
| KC$_2$ | 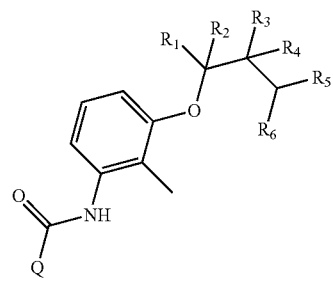 | 100 | 40 | — |

We claim:

1. An amide compound as represented by the general formula I:

I wherein:
R$_1$ is C$_1$-C$_6$ alkyl, (C$_1$-C$_6$) alkoxy-(C$_1$-C$_6$) alkyl, (C$_3$-C$_8$) alkenyloxy-(C$_1$-C$_6$) alkyl, (C$_3$-C$_8$) alkynyloxy-(C$_1$-C$_6$) alkyl, aryl-(C$_1$-C$_6$) alkoxy-(C$_1$-C$_6$) alkyl substituted by at most 6 (1-6) the same or different R$_7$, C$_1$-C$_6$ alkoxycarbonyl, (C$_3$-C$_6$) cycloalkyl-(C$_1$-C$_6$) alkoxycarbonyl, C$_1$-C$_6$ alkylaminocarbonyl, arylaminocarbonyl or aryl-(C$_1$-C$_6$) alkylaminocarbonyl;
wherein aryl is benzene, 5- or 6-membered heterocyclic ring with 1 to 3 heteroatoms or a 5- or 6-membered benzoheterocyclic ring with 1 to 3 heteroatoms;
R$_2$ and R$_4$ are H;
R$_3$ and R$_5$ are independently of one another represent H, halogen, CN, C$_1$-C$_{12}$ alkyl or C$_1$-C$_{12}$ haloalkyl;
R$_6$ is C$_2$-C$_{12}$ alkyl;
R$_7$ is halogen, nitro, CN, C$_1$-C$_6$ alkyl or C$_1$-C$_6$ haloalkyl;
Q is Q$_1$ R$_8$ is C$_1$-C$_3$ alkyl, C$_1$-C$_3$ haloalkyl or C$_3$-C$_6$ cycloalkyl;
R$_9$ is H, halogen or methyl;
R$_9$ is not H, when R$_8$ is difluoromethyl.

2. An amide compound according to claim 1, characterized in general formula I wherein:
R$_1$ is C$_1$-C$_6$ alkyl;
R$_2$ and R$_4$ are H;
R$_3$ and R$_5$ are independently of one another represent H, F, C$_1$-C$_3$ alkyl or C$_1$-C$_3$ haloalkyl;
R$_6$ is C$_2$-C$_6$ alkyl;
Q is Q$_1$;
R$_8$ is methyl, ethyl, n-propyl, i-propyl, trifluoromethyl, difluoromethyl, pentafluoroethyl, heptafluoroisopropyl or cyclopropyl;
R$_9$ is H, F, Cl, Br, I or methyl;
R$_9$ is not H, when R$_8$ is difluoromethyl.

3. An amide compound according to claim 2, characterized in general formula I wherein:
R$_1$ is methyl;
R$_2$, R$_3$, R$_4$ and R$_5$ are independently of one another represent H;
R$_6$ is ethyl or n-propyl;
when Q is Q$_1$;
R$_8$ is methyl or difluoromethyl;
R$_9$ is Cl.

4. A process for preparing the compound of claim 1, comprising:
1) contacting a compound having formula II with a compound having formula III to form a compound having formula I as follows:

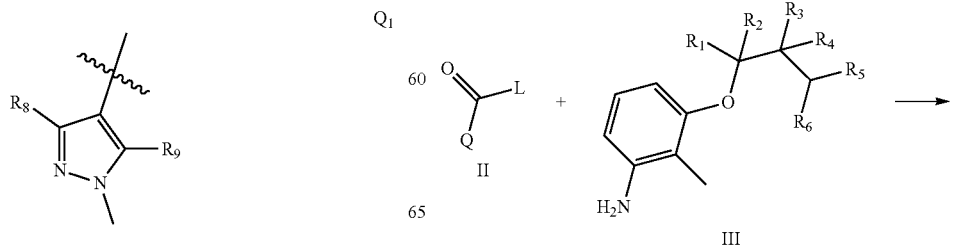

-continued

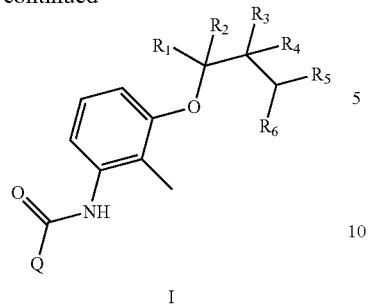

I or
2) contacting a compound having formula II with a compound having formula IV to form a compound having formula V, and then contacting the compound having formula V with a compound having formula VI to form the compound having formula I as follows:

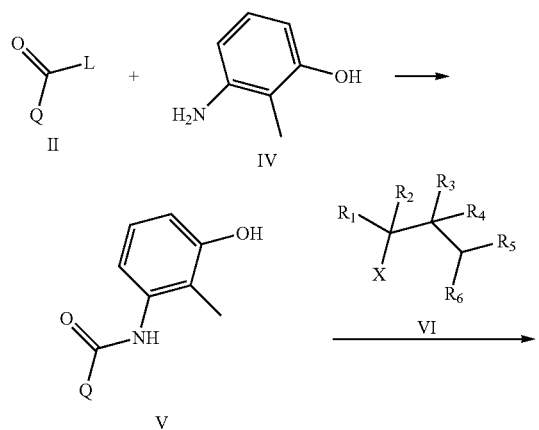

-continued

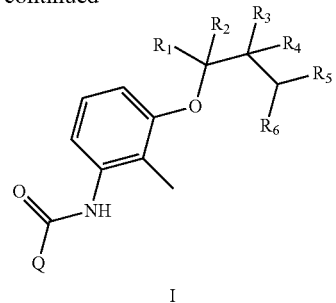

I wherein:

L is a leaving group, X is a halogen; $R_1$, $R_2$, $R_3$, $R_4$, $R_5$ and $R_6$ are as defined above.

5. A method for controlling fungal disease comprising applying a compound of general formula I according to claim 1 to fungi on a plant surface or a growth medium.

6. A fungicidal composition comprising an effective amount of a compound of claim 1 and an acceptable carrier, where the effective amount is 1%-99% by weight.

7. A method for controlling fungal diseases comprising applying the composition of claim 6 the fungi on a plant surface or in a growth medium, where the effective amount is within a range of from 10 g/ha to 1000 g/ha.

8. A method of claim 5 wherein the fungal disease is selected from corn rust, anthracnose of cucumber or cucumber downy mildew.

9. A method of claim 7 wherein the fungal disease is selected from corn rust, anthracnose of cucumber or cucumber downy mildew.

10. The method of claim 5 wherein the compound of general formula I is applied directly to the plant surface.

* * * * *